US011174357B2

(12) United States Patent
Provonchee et al.

(10) Patent No.: US 11,174,357 B2
(45) Date of Patent: Nov. 16, 2021

(54) CROSSLINKED POLYSACCHARIDES AND RELATED METHODS

(71) Applicant: Advanced Aesthetic Technologies, Inc., Brookline, MA (US)

(72) Inventors: Richard Provonchee, Cushing, ME (US); Valentino Gitto, Johor Bahru (MY); Leonard Miller, Chestnut Hill, MA (US)

(73) Assignee: ADVANCED AESTHETIC TECHNOLOGIES, INC., Brookline, MA (US)

( * ) Notice: Subject to any disclaimer, the term of this patent is extended or adjusted under 35 U.S.C. 154(b) by 0 days.

(21) Appl. No.: 16/723,206

(22) Filed: Dec. 20, 2019

(65) Prior Publication Data

US 2020/0216621 A1 Jul. 9, 2020

Related U.S. Application Data

(60) Provisional application No. 62/783,630, filed on Dec. 21, 2018.

(51) Int. Cl.
| | |
|---|---|
| C08F 2/46 | (2006.01) |
| C08F 2/50 | (2006.01) |
| C08G 61/04 | (2006.01) |
| C08J 3/075 | (2006.01) |
| C08J 3/24 | (2006.01) |
| C08J 3/28 | (2006.01) |
| A61K 8/04 | (2006.01) |
| A61Q 19/08 | (2006.01) |
| A61K 8/73 | (2006.01) |

(52) U.S. Cl.
CPC .............. *C08J 3/075* (2013.01); *C08J 3/24* (2013.01); *C08J 3/28* (2013.01); *A61K 8/042* (2013.01); *A61K 8/73* (2013.01); *A61Q 19/08* (2013.01); *C08J 2305/12* (2013.01); *C08J 2405/08* (2013.01)

(58) Field of Classification Search
CPC ....... C08J 3/075; C08J 3/28; C08J 3/24; C08J 2405/08; C08J 2305/12; A61K 8/735; A61K 8/042; A61K 8/73; A61K 2800/12
USPC ........................................... 522/88, 1; 520/1
See application file for complete search history.

(56) References Cited

U.S. PATENT DOCUMENTS

| | | | |
|---|---|---|---|
| 4,684,558 A | 8/1987 | Keusch et al. | |
| 6,031,017 A | 2/2000 | Waki et al. | |
| 2009/0035344 A1* | 2/2009 | Thomas | ................... C08J 3/075 424/423 |
| 2013/0078299 A1* | 3/2013 | Harriton | .............. A61K 9/7053 424/443 |

FOREIGN PATENT DOCUMENTS

WO 2018213408 A1 11/2018

OTHER PUBLICATIONS

Roach et al., Agarose Hydrogel Characterization for Regenerative Medicine Applications: Focus on Engineering Cartilage, Oct. 14, 2016 (Year: 2016).*
Chengan Chiang, "Intravenous Hyaluronidase with Urokinase as Treatment for Arterial Hyaluronic Acid Embolism", Journal, 2015, 114-121, vol. 137, No. 1, Plastic and Reconstructive Surgery, American Society of Plastic Surgeons.
Dr. Omer Buhsem, "Material Method of Study", Jul. 9, 2018.
Wikipedia, "Agar", 1-8, Wikipedia.
Fumio Yoshii, "Hydrogels of Polysaccharide Derivatives Crosslinked with Irradiation at Paste-Like Condition", 2003, 320-324, vol. 208, Nuclear Instruments and Methods in Physics Research B, Elsevier.

* cited by examiner

*Primary Examiner* — Jessica Whiteley
(74) *Attorney, Agent, or Firm* — Hayes Soloway PC

(57) ABSTRACT

Methods of forming cross-linked polysaccharides are disclosed in which one or more polysaccharides are dissolved in solution, gelled, modified to have a desired concentration, and subsequently irradiated. The irradiation of the gel crosslinks the polysaccharide(s) present. The disclosed techniques may be applied to various polysaccharides, including but not limited to agarose and/or hyaluronic acid.

18 Claims, 2 Drawing Sheets

CROSSLINKED POLYSACCHARIDES AND RELATED METHODS

CROSS-REFERENCE TO RELATED APPLICATION

This application claims the benefit of U.S. provisional application Ser. No. 62/783,630, filed Dec. 21, 2018, the contents of which are incorporated by reference herein.

BACKGROUND

Crosslinking is the process of chemically joining two or more polymer chains together through a covalent or ionic bond. Various mechanical properties of a polymer can be modified by crosslinking. For example, crosslinking a material to a low crosslink density can decrease the viscosity of polymer melts, while crosslinking to an intermediate crosslink density can transform a gummy polymer into a material with elastomeric properties and potentially high strength. In some cases, very high crosslink densities can cause a material to become rigid or glassy. Numerous crosslinking techniques are known, including processes that rely on heat, pressure, change in pH, or radiation to initiate the crosslinking process.

SUMMARY

This disclosure relates to methods of crosslinking polysaccharides as well as the resulting crosslinked compositions. In particular, the subject disclosure describes methods of irradiating polysaccharides, particularly agarose, while in a gelled state to achieve a desired level of crosslinking.

As used herein, the term "polysaccharide" refers to a polymeric carbohydrate having the general formula $C_x(H_2O)_y$, such as, for example, starch, dextrin, cellulose, hemicellulose, polydextrose, inulin, beta-glucan, pectin, psyllium husk mucilage, mannan, beta-mannan, carob, fenugreek, guar, tara gum, glucomannan, gum acacia, karaya, tragacanth, arabinoxylan, gellan, xanthan, alginate, agarose, carrageenan, agar, hyaluronic acid, chitin, and chitosan. Many example embodiments in which the polysaccharide agarose is used are described in detail herein. However, the subject disclosure is not intended to be so limited. Specifically, although examples in which agarose is used, any other suitable type of polysaccharide may alternatively or additionally be used. For example, embodiments in which hyaluronic acid is used are also of interest and described in detail herein.

Although irradiation techniques have previously been applied to some polysaccharides for crosslinking purposes, this type of crosslinking process (as previously performed) has many disadvantages. In particular, at low concentrations in water, most polysaccharides will degrade from the effects of irradiation. Degradation can also occur if the polysaccharide is irradiated in a dry state (i.e., with a water concentration of less than 5%). Crosslinking of the polysaccharide thus occurs with only minimal or no degradation within a particular concentration range. Below or above such a concentration of polysaccharide, degradation can occur and may be quite significant. Degradation of the polysaccharide can take various forms, including breakage of one or more glycosidic linkages of the polysaccharide. As set forth more fully below, techniques are described herein to facilitate competitive crosslinking of polysaccharides, particularly agarose, as well as other polysaccharides, such as hyaluronic acid.

Previous attempts at crosslinking polysaccharides by irradiation generally involved irradiating the polysaccharide while in a paste-like state. As used herein, the term "paste-like" refers to a polysaccharide with a water concentration less than about 90% by weight and/or volume. As opposed to gelled polysaccharides, which have a somewhat ordered structure, paste-like polysaccharides do not necessarily have an ordered structure and can exhibit non-uniform mechanical properties throughout. As explained more fully herein, irradiating a polysaccharide in an ordered gel state by irradiation may produce a uniquely crosslinked structure as opposed to irradiating a paste-like polysaccharide.

It is important to note that, to the knowledge of the subject inventor(s), agarose has not previously been crosslinked by irradiation techniques. There are a few reasons that the disclosed techniques have been not been attempted. Firstly, the particular concentration range of agarose needed to facilitate crosslinking as opposed to degradation is difficult to achieve. Also, there previously had been limited use for agarose gels having an agarose concentration within the useful range for crosslinking via irradiation. Thus, the disclosed compositions and techniques are believed to be new and have not previously been easily achievable. Additionally, the present disclosure describes new beneficial uses for the described irradiated and crosslinked agarose materials, which were previously unknown.

Crosslinked polysaccharides have many useful properties. For example, crosslinked agarose is significantly more robust than non-crosslinked agarose. Accordingly, crosslinked agarose has promising potential for uses in many applications, including as dermal filler, cartilage replacement, sutures, surgical fabric, wound care materials, tissue and bone scaffolding, and/or drug delivery vehicles. Crosslinking agarose in gel form via irradiation also provides a number of advantages which may only be possible using the disclosed techniques. For example, the disclosed techniques may provide: good control over agarose concentration, a wide range of various agarose concentrations, and/or gel that can be formed in a predictable size and shape. As described in more detail below, gels and other articles formed from the disclosed crosslinked agarose may be used for any purpose, including cosmetic, reconstructive, and/or therapeutic applications.

BRIEF DESCRIPTION OF THE DRAWINGS

The present disclosure may be more fully understood with reference to the accompanying drawings.

DETAILED DESCRIPTION

Figure 1:
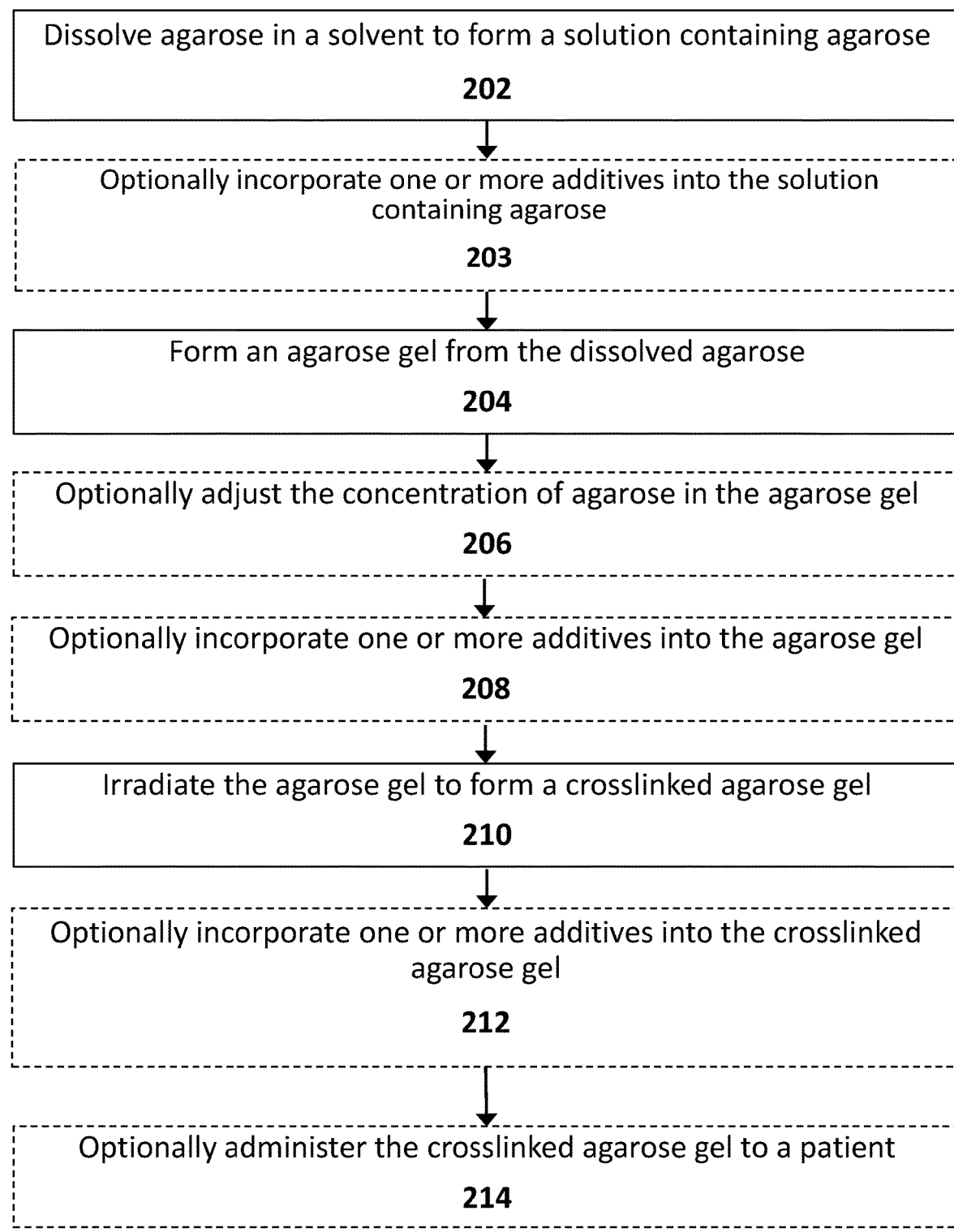
FIG. 1 illustrates an exemplary method of preparing a crosslinked agarose gel, in accordance with various embodiments of the subject disclosure.

As shown in FIG. 1, method 200 includes dissolving agarose in a solvent to form a solution containing agarose (Block 202). As used herein, the term "agarose" refers to a compound based on the following polymeric structure:

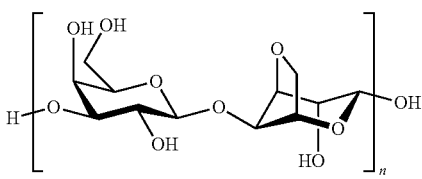

The agarose used in the disclosed methods and compositions may be commercially obtained or prepared by a user. The disclosed agarose may, in some embodiments, include one or more crude, purified, derivatized or modified agars or agaroses. For example, in certain embodiments, the agarose is selected from agarose, purified agarose, modified agarose, and derivatized agarose. The agarose may also be used as mixtures with other compatible polymers and additives such as agar, carrageenan, chitosan, alginate, gelatin, hyaluronic acid, collagen, in some embodiments. In select embodiments, the agarose is unmodified or modified agarose, and/or derivatized agarose. In certain embodiments, the agarose is Gracilaria-derived agarose. Gracilaria-derived agarose has a higher methoxy content than agarose derived from other sources (e.g., Gelidium). Agaroses from other seaweeds, for example, Pterocladia or Gelidiella may also be used as the disclosed agarose.

Any suitable solvent may be used to dissolve the agarose. For example, in some embodiments, the agarose may be dissolved in water with or without non-aqueous liquid(s) present. Example non-aqueous liquids that may be used include but are not limited to glycerine and a glycol. In some embodiments, the agarose may be dissolved in sufficient solvent to produce a solution with at least 1%, 3%, 5%, 10%, 12%, 15% or more agarose by weight. In these and other embodiments, a solution having between 1% and 15%, between 3% and 10%, or approximately 5% agarose by weight may be prepared. In some embodiments, the solvent may be heated to facilitate dissolution of the agarose.

If appropriate for the intended application, one or more additives may also be added to the solution containing agarose (Block 203). If present, additives in liquid and/or solid form may be added to the solution containing agarose. In some embodiments, (crosslinked or non-crosslinked) hyaluronic acid may be added to the solution containing agarose. In some such embodiments, the hyaluronic acid may be added as a solution or particles to the solution containing agarose. In these and other embodiments, hydroxyapatite may be added to the solution containing agarose. Hydroxyapatite may be especially useful as an additive in embodiments in which the resulting crosslinked agarose gel is to be used for dermal filling applications, bone tissue engineering, and the like. Other example additives that may be used include porons, such as particles, beads, threads, rods, or other possible structures. In some such embodiments, the porons may be incorporated into the gel and may thereafter be physically removed from the gel or dissolved and leached from the gel after it has formed to create pores and/or passages within the gel.

Method 200 continues with forming an agarose gel from the dissolved agarose (Block 204). The dissolved agarose may be gelled according to any known technique, including chemical crosslinking. In some embodiments, gelling may be accomplished by filling a mold or other casting device with a solution containing agarose and allowing the solution to gel. In some embodiments, the agarose may be gelled at a room temperature, or a temperature higher or lower than room temperature. After gelling, the agarose gel may have an agarose concentration of at least 0.1%, 1%, 3%, 5%, 7%, 10%, 12%, 15%, or more by weight.

In some embodiments, forming an agarose gel (Block 204) includes gelling the solution containing agarose as a foam or as an open matrix structure. In select embodiments, the solution containing agarose is applied as a coating on an implant or other substrate and then gelled while on the substrate. In these and other embodiments, the solution containing agarose may be imbibed into an absorbent material (e.g., a bandage or sponge) and then gelled on and/or in the absorbent material. In select embodiments, the solution containing agarose may be gelled via an extrusion process, thereby forming a gel having a well-defined structure (e.g., threads, rods, tubes, or other structures having a desired cross-section). In these and other embodiments, the solution containing agarose may be gelled as beads.

Method 200 continues with optionally adjusting the concentration of agarose in the agarose gel (Block 206). As previously explained, agarose gels may be crosslinked by irradiation to yield crosslinked agarose gels with numerous advantageous properties. Without wishing to be bound by theory, it is believed that crosslinking by irradiation is best suited for agarose gels having a particular agarose concentration. For example, agarose gels having an agarose concentration of between 10% and 80% are believed to be within a desirable range to crosslink by irradiation techniques. Method 200 thus includes the optional step of adjusting the agarose concentration in the gel, if desired, to be within a range well-suited to crosslinking by irradiation. In some embodiments, the agarose concentration may be adjusted to be between 10% and 80% by weight. In these and other embodiments, the agarose concentration may be adjusted to be between 20% and 60%, between 30% and 50%, or between 35% and 45% by weight. The agarose concentration of the gel may be adjusted using any suitable technique. For example, in some embodiments, the agarose gel may be fully or partially dehydrated. In some such embodiments, the partially or fully dehydrated agarose gel may be rehydrated (partially or fully) to achieve the desired agarose concentration.

Method 200 continues with optionally incorporating one or more additives into the agarose gel (Block 208). Example additives and relative weight percentages can be any additives previously discussed herein. In particular embodiments, hyaluronic acid (HA) is incorporated into the agarose gel. Without wishing to be bound by theory, the HA may crosslink with itself and/or with the agarose during processing, which may produce a crosslinked gel composition having unique properties. Such a gel may also be affected by exposure to hyaluronidase. It should be noted that if one or more additives are incorporated into the agarose gel, the one or more additives may be added prior to or after adjusting the concentration of agarose in the agarose gel (pursuant to Block 206), if the agarose concentration is adjusted.

Method 200 continues with irradiating the agarose gel to form a crosslinked agarose gel (Block 210). The agarose gel may be irradiated using any suitable technique, such as processes that employ gamma radiation, x-ray or beta radiation (e.g., electron beam "e-beam" processing). Numerous types of irradiating devices are known in the art and may be used to irradiate agarose gel according to the disclosed methods. The agarose gel may be irradiated with any suitable amount of radiation, depending on the desired specifications of the resulting crosslinked agarose gel. For example, in some embodiments, the agarose gel may be dosed with at least 5 kilograys (kGy), 10 kGy, 20 kGy, 30 kGy, 40 kGy, 50 kGy, 60 kGy, 70 kGy, 80 kGy, 90 kGy, 100 kGy, or more. In select embodiments, the agarose gel is irradiated with between 10 and 100 kGy, between 20 and 80 kGy, or between 40 and 60 kGy.

The resulting agarose gel crosslinked via the disclosed irradiation process may have various mechanical properties. For example, in some embodiments, the crosslinked agarose gel may exhibit increased strength as compared to an agarose gel formed according to the same technique that has not been crosslinked. Additionally, the crosslinked agarose gel may, in some embodiments, no longer be thermally reversible. In other words, the crosslinked agarose gel may not melt upon exposure to an amount of heat that would cause a similar non-crosslinked agarose gel to melt. Numerous other mechanical properties of the disclosed crosslinked agarose gel are possible and contemplated herein.

Method 200 of FIG. 1 includes optionally incorporating one or more additives into the crosslinked agarose gel (Block 212). One or more additives may be incorporated into the crosslinked agarose gel if, for example, the additive(s) might not tolerate irradiation. In embodiments in which the one or more additives incorporated into the crosslinked agarose gel are in liquid form, the one or more additives may be infused into the gel. In embodiments in which the one or more additives incorporated into the crosslinked agarose gel are solid(s), the one or more additives may be loaded into the gel matrix. Example liquid additives include but are not limited to pharmaceutical agents or other types of beneficial agents. Example solid additives include but are not limited to cells, tissue, pharmaceutical and/or beneficial agents.

Method 200 of FIG. 1 concludes with optionally administering the crosslinked agarose gel to a patient (Block 214). The disclosed crosslinked agarose gels may be administered in any desired structure. For example, in some embodiments, the crosslinked gels may be used as is, such as in the form of sheets, threads, rods, cast structures, matrices, or other defined structures. In these and other embodiments, the crosslinked agarose gels may be ground or chopped to create smaller pieces or particles. In further embodiments, the crosslinked agarose gels may first be dehydrated and then used as is or chopped or ground up after dehydration. In yet other embodiments, the disclosed crosslinked agarose gels may be combined with non-crosslinked gels or other materials to create hybrid structures. Numerous configurations and variations are possible and contemplated herein.

In some embodiments, the crosslinked agarose gel is administered to a patient transdermally via a needle. In some such embodiments, the gel may be prepared for use by an aseptic fill process (e.g., a process in which the agarose gel is loaded into a delivery device in a sterile manner). In embodiments in which an aseptic fill process is used, there may be no need for a terminal sterilization step to occur in which the agarose gel is sterilized after at least some packaging has taken place. The delivery technique can be selected based on the intended use of the crosslinked agarose gel. In select embodiments, the crosslinked agarose gel may be used for dermal fill, reconstruction, and/or scaffolding applications. In select embodiments, the disclosed agarose gels are used for one or more of the following: filling in wrinkles, fine lines, or deep creases, improving skin imperfections, such as scars, adding volume to lips or cheeks, contouring the jaw line, or adjusting the appearance of any other body part, such as rhinoplasty. Countless other uses for the disclosed crosslinked agarose gels are possible and contemplated herein.

In some embodiments, the disclosed agarose gel compositions are administered to a patient at concentrations of at least 2%, 3%, 4%, 5%, 6%, 7%, 8%, 9%, or 10% by weight.

In these and other embodiments, the agarose gel crosslinked by irradiation may be mixed with one or more other types of hydrogels. For example, in some embodiments, hyaluronic acid (HA) is mixed with the crosslinked agarose gel prior to administration to a patient.

The disclosed techniques and compositions may provide numerous advantages over alternative preparation and sterilization procedures. Notably, crosslinking an agarose by irradiating an agarose gel having a concentration within a desired range can produce a robust crosslinked agarose well-suited to application within the human body. Agarose gels prepared according to the disclosed methods may have improved tactile effects in the body. For example, the disclosed agarose gels (formed from an agarose gel crosslinked by irradiation) may be firmer than conventional agarose gels. Agarose gels prepared according to the disclosed methods may, in some embodiments, be sterilizable by heat without significant loss of gel structure. Due to the nature of the presently disclosed agarose gels, agarose gels crosslinked by the disclosed techniques may have increased overall residence time in the body, thereby affording additional time before follow-up procedures are needed to replenish gel that is consumed by the body.

Example Embodiments with Hyaluronic Acid

As previously explained, although numerous examples are disclosed in which agarose is used as the polysaccharide crosslinked by irradiation, the subject disclosure also extends to embodiments in which other polysaccharides are crosslinked via irradiation techniques while in a gelled state. For example, in some embodiments, a hyaluronic acid gel is formed and subsequently irradiated to form a crosslinked hyaluronic acid gel. Method 300 of FIG. 2 describes an example method of crosslinking a hyaluronic acid gel using irradiation techniques.

Figure 2:
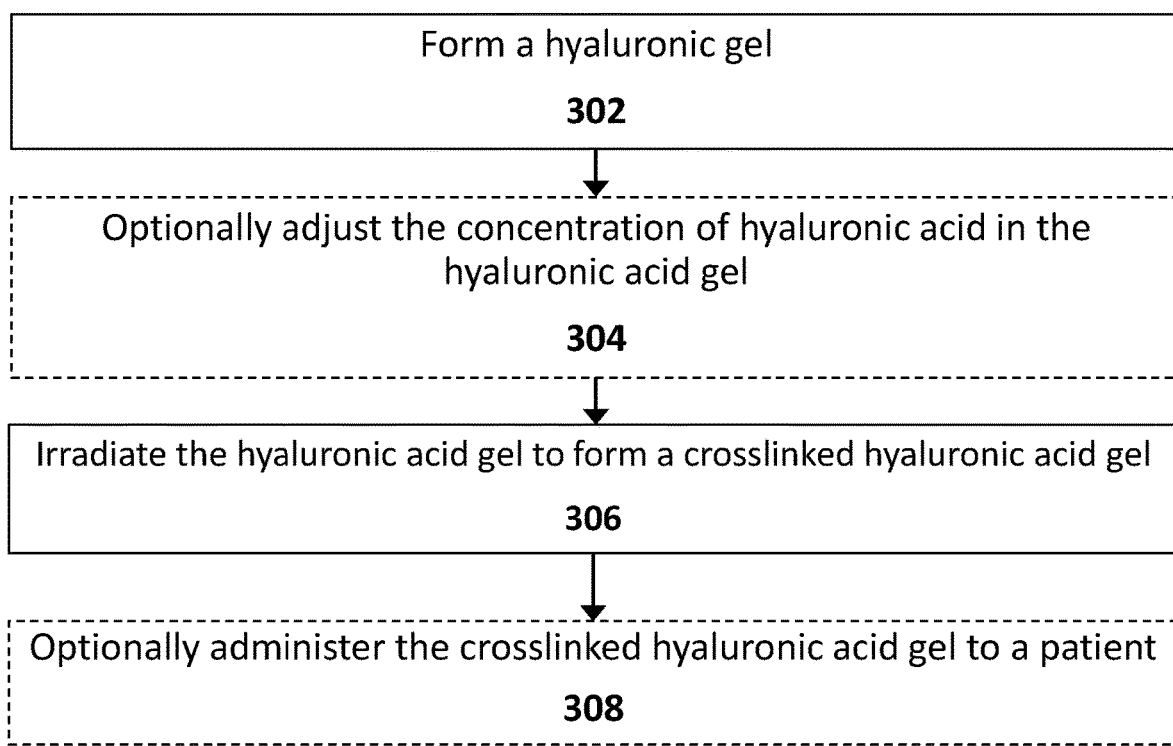
FIG. 2 illustrates an exemplary method of preparing a crosslinked hyaluronic acid gel, in accordance with various embodiments of the subject disclosure.

As shown in FIG. 2, method 300 includes forming a hyaluronic gel (Block 302). Forming a hyaluronic acid gel can be accomplished using any suitable method known to those skilled in the art. Method 300 continues with optionally adjusting the concentration of hyaluronic acid in the hyaluronic acid gel Block 304). If performed, the concentration of hyaluronic acid may be adjusting using any technique described herein with respect to Block 206 of method 200. Additionally, the concentration of hyaluronic acid may be adjusted to any concentration previously described for agarose in method 200 (e.g., 10%-80%, 20%-60%, 30%-50%, or 35%-45% by weight). The hyaluronic acid gel may then be irradiated to form a crosslinked hyaluronic acid gel (Block 306). Any technique may be used to irradiate the hyaluronic acid gel, including techniques described in method 200, Block 210. One or more additives may optionally be incorporated into the hyaluronic acid gel prior to or after irradiation, as desired. Any additives previously discussed herein may be incorporated into the hyaluronic acid gel. The crosslinked hyaluronic acid gel may then be administered to a patient (Block 308). Any appropriate administration technique may be used to administer the crosslinked hyaluronic acid gel to a patient, including those previously discussed with respect to Block 214 of method 200.

Example Embodiments with Agarose and Hyaluronic Acid

A particular example embodiment in which a mixture of agarose gel and hyaluronic acid is crosslinked via irradiation is described in detail below.

Hyaluronic acid (that has not been crosslinked) tends to form a thick, gel-like solution, even at relatively high concentrations. In contrast to an agarose gel, which adopts the particular shape/structure in which it was gelled, hyaluronic acid behaves more like a viscous solution and adopts the shape of a vessel in which it is contained. In other words, while agarose gels can typically retain a given shape or structure, hyaluronic acid gels tend to be more malleable. While crosslinking hyaluronic acid via irradiation may have useful applications, these applications may not require the crosslinked hyaluronic acid to have a well-defined structure or shape. However, a mixture of agarose and hyaluronic acid may form a gel having a defined structure and, after adjusting the water content to a suitable amount (if necessary) the mixture of agarose gel and hyaluronic acid may be crosslinked via irradiation (using any of the techniques previously described herein) to form a crosslinked gel having a defined shape/form. Without wishing to be bound by theory, it is believed that a gel containing agarose and hyaluronic acid that is crosslinked via irradiation may have a gel matrix that exhibits unique properties.

To produce a crosslinked gel containing agarose and hyaluronic acid, a solution containing agarose and hyaluronic acid may be created. For purposes of illustration, a solution containing between 1 and 2% agarose by weight and approximately 6% hyaluronic acid by weight may be produced. However, in other embodiments, the concentrations of agarose and/or hyaluronic acid may be increased or decreased and/or the relative concentrations of each may be altered. The solution may then be gelled to form a particular shape or structure. After gel formation, the gel may be partially dehydrated to have an agarose and hyaluronic acid concentration within an acceptable range to crosslink using irradiation. The gel may then be irradiated to crosslink the agarose and hyaluronic acid. In this example embodiment, crosslinks may form between agarose chains, between hyaluronic acid chains, and/or between agarose chains and hyaluronic acid chains. Numerous configurations and variations are possible. The crosslinked gel may then be partially rehydrated (if desired) and administered to a patient with or without additional further processing. Additionally, in some embodiments, the crosslinked gel may be exposed to a hyaluronidase enzyme to degrade the hyaluronic acid in the crosslinked gel. In some such embodiments, the resulting gel may retain its form or shape even after the hyaluronic acid has been partially or fully degraded. In other embodiments, the resultant gel may lose some or all of its strength, form or shape after the hyaluronic acid has been partially or fully degraded.

The features and advantages described herein are not all-inclusive and, in particular, many additional features and advantages will be apparent to one of ordinary skill in the art in view of the present disclosure. Persons skilled in the relevant art can appreciate that many modifications and variations are possible in light of the above disclosure.

The invention claimed is:

1. A method of forming a crosslinked agarose gel, the method comprising:
    dissolving an agarose in a solvent to form a solution containing agarose;
    gelling the solution containing agarose to form a gelled agarose;
    modifying the gelled agarose to have an agarose concentration of between 10% and 80%;
    irradiating the gelled agarose having an agarose concentration of between 10% and 80% to form a crosslinked agarose gel.

2. The method of claim 1, wherein the agarose is selected from the group consisting of: purified agarose, modified agarose, and derivatized agarose.

3. The method of claim 1, wherein the solvent comprises water.

4. The method of claim 3, wherein the solvent comprises glycerine or a glycol.

5. The method of claim 1, wherein modifying the gelled agarose comprises at least partially dehydrating the gelled agarose to yield a gelled agarose having an agarose concentration of between 10% and 80%.

6. The method of claim 1, wherein the gelled agarose has an agarose concentration of between 20% and 60%.

7. The method of claim 1, wherein irradiating is accomplished by exposure to one or more of the following: gamma radiation, x-rays, or beta radiation.

8. The method of claim 1, wherein the gelled agarose is irradiated with at least 5 kilograys (kGy) of radiation.

9. The method of claim 1, further comprising administering the crosslinked agarose gel to a patient.

10. The method of claim 9, further comprising mixing the crosslinked agarose gel with hyaluronic acid prior to administering to the patient.

11. The method of claim 1, wherein gelling the solution containing agarose to form a gelled agarose comprises gelling the solution containing agarose as a foam or as an open matrix structure.

12. The method of claim 1, wherein gelling includes applying the solution containing agarose as a coating on a substrate and then gelling the solution while on the substrate.

13. The method of claim 1, wherein gelling includes imbibing the solution containing agarose into an absorbent material and then gelling the solution containing agarose on or in the absorbent material.

14. The method of claim 1, wherein gelling the solution containing agarose is accomplished through an extrusion process.

15. The method of claim 1, further comprising incorporating one or more additives into the crosslinked agarose gel.

16. The method of claim 15, wherein the one or more additives are selected from the group consisting of pharmaceutical or beneficial agents, cells, and tissue.

17. The method of claim 1, further comprising incorporating one or more additives into the solution containing agarose.

18. The method of claim 17, wherein the one or more additives comprise hyaluronic acid.

* * * * *